United States Patent [19]

Warriner

[11] Patent Number: Plant 5,684

[45] Date of Patent: Mar. 11, 1986

[54] ROSE PLANT JACAVE

[75] Inventor: William A. Warriner, Tustin, Calif.

[73] Assignee: Jackson & Perkins Company, Medford, Oreg.

[21] Appl. No.: 549,299

[22] Filed: Nov. 7, 1983

[51] Int. Cl.[4] ..... A01H 5/00

[52] U.S. Cl. ..... Plt./22

[58] Field of Search ..... Plt./22

*Primary Examiner*—James R. Feyrer

*Attorney, Agent, or Firm*—Klarquist, Sparkman, Campbell, Leigh & Whinston

[57] ABSTRACT

A floribunda rose variety having vigorous plant which is somewhat susceptible to rose powdery mildew, short bloom cycle in greenhouse conditions, lavender flowers having 30–35 petals, and strong fragrance.

1 Drawing Figure

This present invention relates to a new and distinct variety of rose plant of the floribunda class which was originated by me by crossing the variety Heirloom, U.S. Plant Pat. No. 3,234, with the variety Angel Face, U.S. Plant Pat. No. 2,792.

The primary objective of this breeding was to produce a new rose variety of a lavender color suitable for use as a greenhouse cut flower. This objective was substantially achieved along with other desirable improvements as evidenced by the following unique combination of characteristics which are outstanding in the new variety and which distinguish it from its parents as well as from all other varieties of which I am aware:

1. Short bloom cycle in greenhouse conditions.
2. Lavender color from bud to full open.
3. Strong fragrance.
4. Vigorous plant, somewhat susceptible to rose powdery mildew.
5. Petal count of 30 to 35 thick petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Heirloom, U.S. Plant Pat. No. 3,234.

*Pollen parent.*—Angel Face, U.S. Plant Pat. No. 2,792.

Classification:

*Botanical.*—Rosa hybrid.

*Commercial.*—Floribunda.

FLOWER

Observations made from specimens grown in a greenhouse at Irvine, Calif. in April.

Blooming habit: Recurrent, continuous.

Bud:

*Size.*—$1\frac{1}{8}''$ to $1\frac{1}{4}''$ when petals start to unfurl.

*Form.*—Blunt top.

*Color.*—When sepals first divide, Red-Purple 59D. When half blown; upper side of petals ranging from Red Group 54A to 54D; lower side of petals ranging from Red Group 54A to 54D with darker areas of Red-Purple 57C.

*Sepals.*—Color: Outer surface Green 138B with few stipitate glands. Three appendaged sepals lightly appendaged. Two unappendaged sepals hairy edged.

*Recpetacle.*—Color: Green 138B. Shape: Funnel. Size: Large, broad. Surface: Smooth.

*Peduncle.*—Length: Medium. Surface: Nearly smooth. Color: Light green. Strength: Stiff, erect.

*Opening.*—Petals fold outward with little curling.

Bloom:

*Size.*—Small. Average open size: 2"–3".

*Borne.*—Singly and several together.

*Stems.*—Long, strong.

*Form.*—When first open, high center. Permanence: Flattens.

*Petalage.*—Number of petals under normal conditions: 30–35.

*Color.*—Center of flower: Upper side of petals Purple 75D; reverse side of petals Purple 75D; base of petals Yellow-Green 154D at small area at point of attachment. General tonality from a distance Purple 75D.

*Variegations.*—Darker areas on outer petals where first exposed to sunlight.

*Discoloration.*—General tonality at end of first day: No change. Third day: Purple 75D.

*Fragrance.*—Strong.

Petals:

*Texture.*—Thick.

*Shape.*—Nearly round.

*Form.*—Tips slightly recurved.

*Arrangement.*—Imbricated. Petaolids in center, few.

*Persistence.*—Drop off cleanly.

*Lastingness.*—On the plant, long. As cut flower, long.

Reproductive parts:

Anthers.—Large, many. Color: Yellow. Arrangement: Regular around styles.

*Filaments.*—Color: Yellow.

*Pollen.*—Lemon yellow.

*Styles.*—Color: Pink.
*Stigmas.*—Color: White.

PLANT

Form: Bush.
Growth: Very vigorous, upright, Bloom cycle is 36 to 40 days in winter months in normal greenhouse conditions at Irvine, Calif.
Foliage: Number of leaflets on normal mid-stem leaves: 5–7.
*Size.*—Large.
*Quantity.*—Normal.
*Color.*—New foliage: Near Greyed Purple 187B. Old foliage: Medium green.
Leaflets:
*Shape.*—Oval pointed.
*Texture.*—Upper side: Leathery.
*Edge.*—Serrated.
*Serration.*—Single, small.
*Petiole.*—Rachis: Color: Green. Underside: Few prickles.
*Stipules.*—Long, bearded.

*Disease resistance.*—Susceptible to mildew under adverse growing conditions at Irvine, Calif.
Wood:
*New wood.*—Color: Reddish. Bark: Smooth.
*Old wood.*—Color: Green. Bark: Smooth.
Prickles:
*Quantity.*—On main stalks from base, few. On laterals from stalk, few.
*Form.*—Long, straight.
*Color when young.*—Red.
*Position.*—Irregular.
Small prickles:
*Quantity.*—On main stalks, none. On laterals, none.

I claim:

1. A new and distinct variety of rose plant of the floribunda class, substantially as herein shown and described, characterized particularly as to novelty by the unique combination of its vigorous plant producing fragrant, lavender flowers suitable for culture in greenhouse conditions for production of cut flowers.

* * * * *

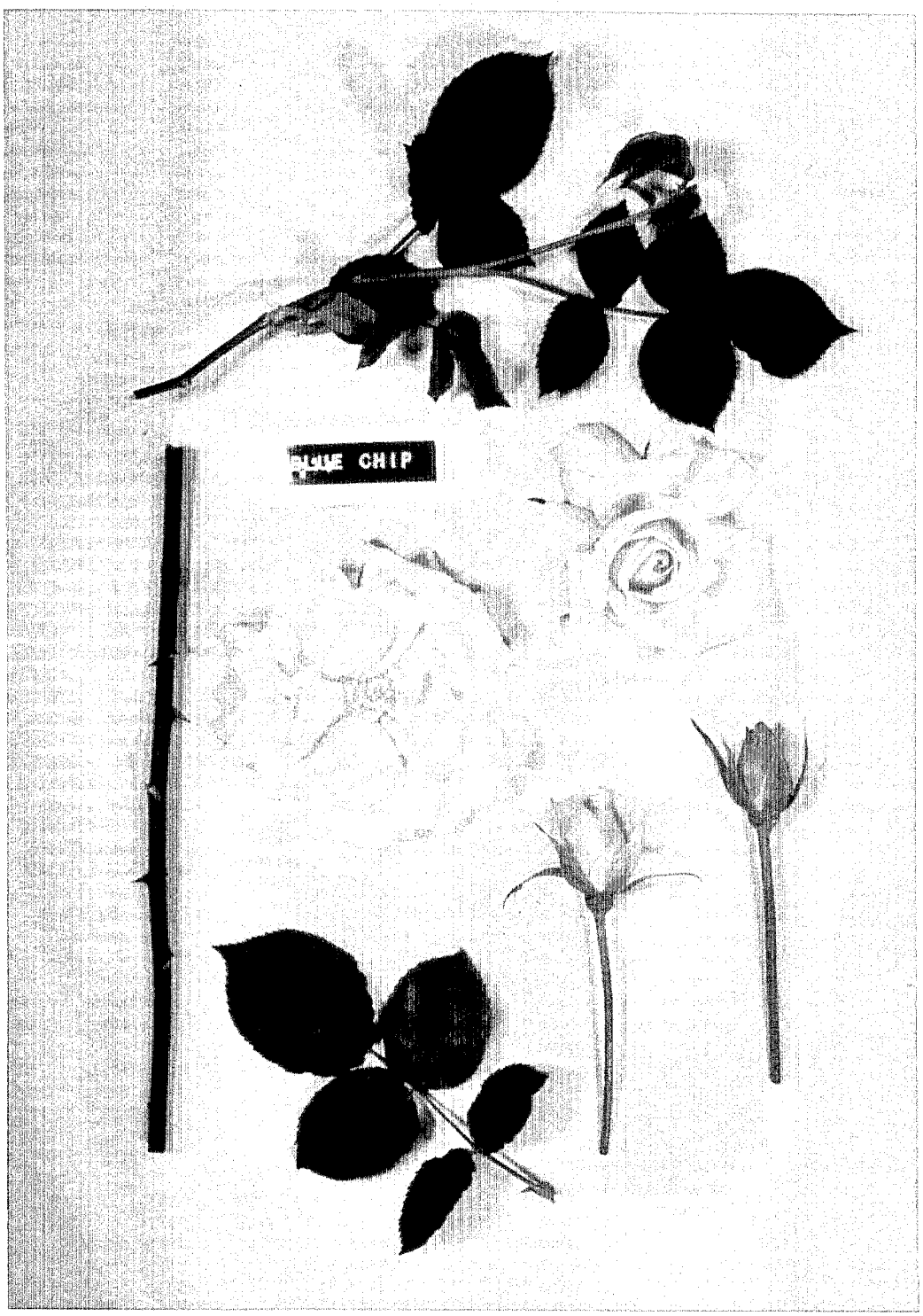
BLUE CHIP